United States Patent [19]

Browne et al.

[11] Patent Number: 4,872,316

[45] Date of Patent: Oct. 10, 1989

[54] SYSTEM FOR MONITORING A LIQUID ENTRAINED IN A FLUID

[75] Inventors: Fredrick D. Browne, Somerville; Jacob H. Martin, Wellesley, both of Mass.

[73] Assignee: The Charles Stark Draper Laboratory, Inc., Cambridge, Mass.

[21] Appl. No.: 151,071

[22] Filed: Feb. 1, 1988

[51] Int. Cl.[4] .................. F25B 49/00; F25B 43/02
[52] U.S. Cl. .................................. 62/129; 62/470; 184/108; 73/863.21; 340/631
[58] Field of Search .............. 62/125, 126, 127, 129, 62/192, 193, 195, 470, 471; 184/6.4, 108; 340/631; 324/61 R, 62; 73/61 R, 61.1 R, 863.21, 863.22, 863.43, 863.52, 863.53, 863.86

[56] References Cited

U.S. PATENT DOCUMENTS

| 4,474,034 | 10/1984 | Avery, Jr. | 62/125 X |
| 4,478,050 | 10/1984 | DiCarlo et al. | 62/470 X |
| 4,490,988 | 1/1985 | Vogel et al. | 62/193 |
| 4,494,413 | 1/1985 | Bukkems et al, | 73/863.43 |
| 4,649,711 | 3/1987 | Sibley et al. | 340/631 X |
| 4,660,414 | 4/1987 | Hatton et al. | 73/61.1 R |

Primary Examiner—Harry B. Tanner
Attorney, Agent, or Firm—Joseph S. Iandiorio

[57] ABSTRACT

A monitoring system for detecting contamination of a liquid entrained in a circulating fluid, including a housing having an inlet for receiving the fluid, a reservoir for containing extracted liquid, and an outlet portion disposed in predetermined relationship with the reservoir for venting the fluid from the housing. There is also a separator, which may be formed as part of the housing, for extracting liquid from the fluid and directing the extracted liquid to the reservoir. A probe, disposed in the reservoir, measures an electrical parameter representative of the electrical resistance of the liquid to detect a change in resistivity indicative of contamination of the liquid.

18 Claims, 4 Drawing Sheets

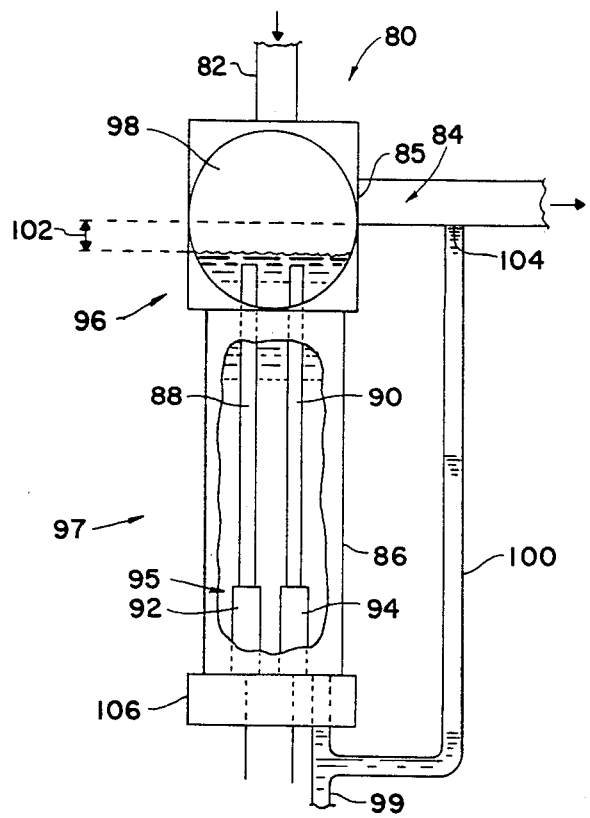
Fig. 5
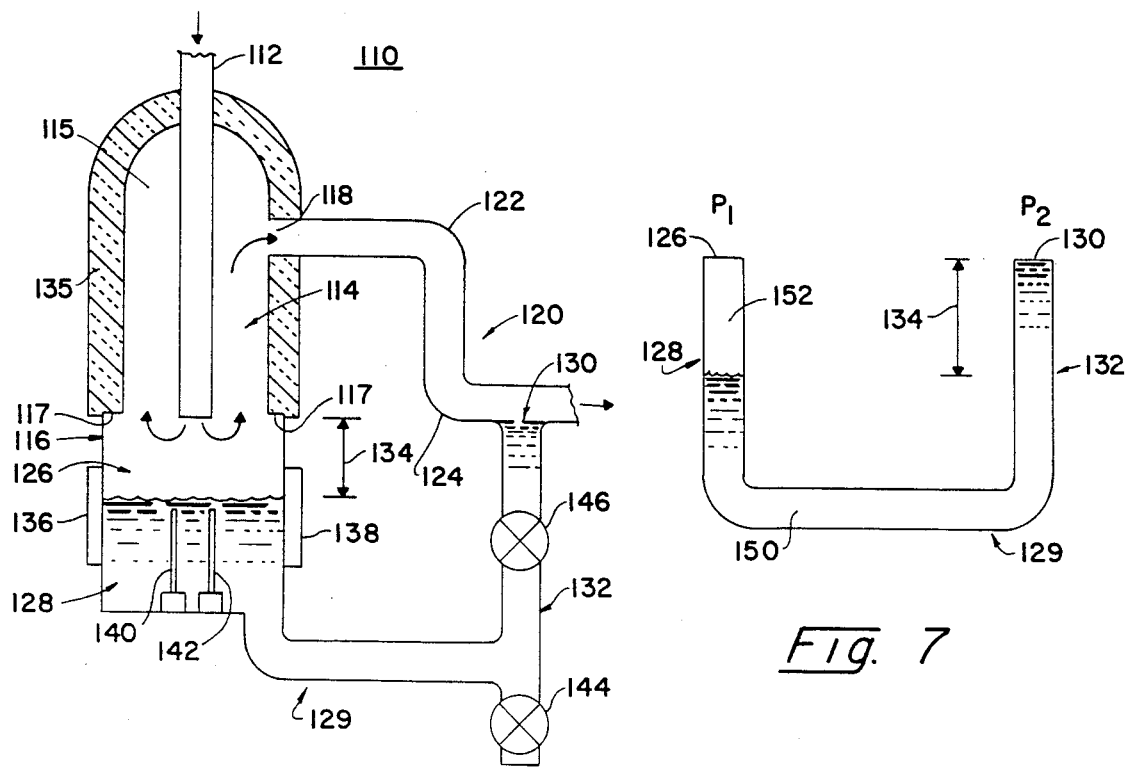
Fig. 6
Fig. 7

SYSTEM FOR MONITORING A LIQUID ENTRAINED IN A FLUID

FIELD OF INVENTION

This invention relates to a system for detecting contamination of a liquid entrained in a circulating fluid and more particularly to a system which continuously extracts portions of the liquid from the fluid, determines a selected parameter such as the electrical resistance of the liquid, and gradually returns the extracted liquid to the fluid.

BACKGROUND OF INVENTION

There are a number of situations in which contamination such as a change in acidity or alkalinity of a fluid circulating within a closed system can damage components within the closed system. In refrigeration systems, for example, lubricating oil is entrained in refrigerant which is circulated by a compressor through a closed set of components. The compressor must be continually provided with lubricant including the entrained lubricating oil. Refrigerants break down over time, however, leading to formation of strong acids or bases which attack the compressor and other critical components of the refrigeration system.

Presently, lubricating oil is monitored by removing samples from the crankcase of the refrigeration compressor. The acidity of the sample is tested remote from the refrigeration system by wet chemical titration or by measurement of resistivity during titration to indicate when neutralization of the lubricant occurs. During sampling, however, the compressor is typically shut down to avoid the hazards of burns, injury from rotating fan blades, and electric shocks associated with working on an operating machine. Further, the oil darkens and becomes increasingly opaque as it becomes contaminated, making it increasingly difficult to detect the end point of titration.

One apparatus for withdrawing oil from a refrigeration system connects across the compressor or condenser and withdraws refrigerant into a chamber. When a quantity of oil has accumulated, the apparatus is disconnected and the oil drained from the chamber. This procedure may well remove enough oil from the system to cause mechanical damage to bearings, pistons and cylinder walls due to inadequate lubrication. Moreover, the oil is not continuously monitored and serious chemical damage may result to refrigeration system components before the sample is taken. Further, any contamination which arises after sampling will not be detected until the next manual sampling procedure.

SUMMARY OF INVENTION

It is therefore an object of this invention to provide a system which automatically monitors a liquid within a circulating fluid.

It is a further object of this invention to provide such a monitoring system which during monitoring enables uninterrupted operation of a closed system through which the fluid circulates.

It is a further object of this invention to provide such a monitoring system which provides remote and continual monitoring of contamination of the liquid.

It is a further object of this invention to provide such a monitoring system which can continually extract the liquid, provide it for sampling, and return it gradually to the circulating fluid.

It is a further object of this invention to provide such a monitoring system which can establish only a slight pressure drop across it.

Yet another object of this invention is to provide an improved system for detecting a change in acidity or alkalinity of lubricating oil entrained in refrigerant.

A still further object of this invention is to provide such a monitoring system which electrically monitors the oil during operation of a refrigeration system to obviate titrations and other chemical testing.

This invention results from the realization that a truly effective system for continuously monitoring contamination of lubricating oil entrained in circulating refrigerant can be achieved by installing a housing in a closed refrigeration system, the housing including a reservoir and an element for separating the oil from the refrigerant, and measuring the resistance between electrodes disposed in the reservoir to detect a change in resistivity when the oil becomes contaminated. It is a further realization of this invention that oil can be continuously extracted, sampled, and returned to the circulating refrigerant by constructing the reservoir to have an intake portion to receive newly extracted oil and an oil return portion through which oil is pumped to gradually rejoin the refrigerant.

This invention features a monitoring system for detecting contamination of a liquid entrained in a circulating fluid. There is a housing having an inlet for receiving the fluid, a reservoir for containing extracted liquid, and an outlet portion disposed in predetermined relationship with the reservoir for venting the fluid from the housing. There are also separating means for extracting liquid from the fluid and directing the extracted liquid to the reservoir, and probe means, disposed in the reservoir, for measuring an electrical parameter representative of the electrical resistivity of the liquid to detect a change in resistivity indicative of contamination of the liquid.

In one embodiment, a separating means directs newly extracted liquid proximate the probe means. The separating means, the reservoir and the outlet portion are arranged relative to each other to establish continual replacement of extracted liquid. The separating means includes a conduit having at least one opening for passing fluid to the outlet portion and a passage below the opening for guiding the extracted liquid to the probe means.

In another embodiment, the reservoir includes an intake portion and a liquid return portion for drawing the extracted liquid from the intake portion of the reservoir and passing the liquid to the outlet portion to mix with the vented fluid. The housing is constructed to establish a decrease in pressure of the fluid between the intake portion and the liquid return portion to pump extracted liquid through the reservoir. The outlet portion is constructed to re-entrain the extracted liquid with the vented fluid. The system may further include sight glass means for viewing the electrodes, and alarm means, responsive to the probe means, for indicating when the probe means detects a change in resistance of the extracted liquid. The separating means may include means for altering the direction of the fluid from the inlet. There may also be means for comparing the measured electrical parameter with a reference level to detect contamination of the liquid. The system may also include means for sensing the temperature of the liquid, and means for adjusting the measured value of the electrical parameter to compensate for changes in resistivity attributable to changes in temperature.

This invention also features a monitoring system, for use within a closed refrigeration system including a compressor, a condenser, and an evaporator, for detecting contamination of a lubricant entrained in refrigerant circulating through the refrigeration system. There is a housing having an inlet for receiving the refrigerant, a reservoir for containing extracted lubricant, and an outlet portion disposed in predetermined relationship with the reservoir for venting the refrigerant to the remainder of the refrigeration system. The system further includes separation means for extracting lubricant from the refrigerant and directing the extracted lubricant to the reservoir. There is also probe means for measuring an electrical parameter representative of the electrical resistance of the lubricant to detect a change in resistivity indicative of contamination of the lubricant. The monitoring system may be disposed on the discharge side or the suction side of the compressor.

This invention further features a monitoring system including a housing having an inlet for receiving circulating fluid having a liquid entrained therein, a reservoir, and an outlet portion. The reservoir is constructed as a conduit having a first opening communicating with an intake portion of the reservoir and a second opening communicating with a liquid return portion connected through the second opening to the outlet portion. There are also means for establishing a decrease in pressure of the fluid between the first and second opening of the reservoir to pump extracted liquid through the reservoir, and means for sampling the extracted liquid.

In one embodiment, the means for sampling includes valve means for withdrawing a sample of the extracted liquid. Alternatively, the sampling includes probe means for measuring a parameter of the liquid such as an electrical parameter representative of the electrical resistance of the liquid. The housing may include means for altering the direction of flow of the fluid from the inlet to extract liquid from the fluid.

DISCLOSURE OF PREFERRED EMBODIMENTS

Other objects, features and advantages will occur from the following description of preferred embodiments and the accompanying drawings, in which:

FIG. 5 is a schematic partial cutaway diagram of an alternate apparatus according to this invention for installation in the refrigeration system of FIG. 1;

FIG. 6 is a schematic cross-sectional diagram of yet another apparatus according to this invention for establishing a greater pressure drop in fluid between the intake portion and the liquid return portion of the reservoir;

FIG. 7 is a schematic diagram of the difference in pressure at the two openings of the reservoir shown in FIG. 6;

This invention may be accomplished by a monitoring system having a housing which receives circulating fluid in which a liquid is entrained, extracts a portion of the liquid and directs the extracted liquid to a reservoir. A probe in the reservoir measures the electrical resistance of the liquid to detect a change in resistivity which indicates that the liquid has become contaminated. Alternatively, liquid in the reservoir is sampled by withdrawing it through a valve.

Preferably, the monitoring system continually extracts liquid from the circulating fluid and gradually returns it to the fluid. The continual replacement of the extracted liquid ensures that the most recent changes in resistivity or other selected parameters such as pH will be monitored.

Figure 1:
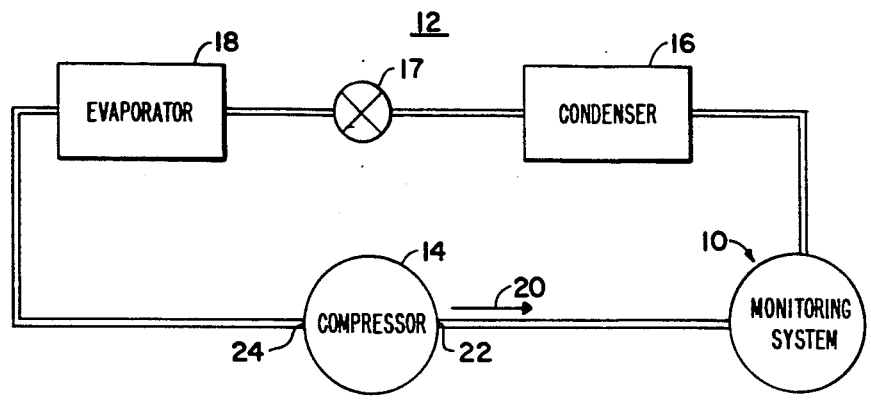
FIG. 1 is a schematic block diagram of a monitoring system according to this invention incorporated in a refrigeration system.

In one application the fluid is a refrigerant, the liquid is lubricant, and the monitoring system is disposed in a closed refrigeration system as shown schematically in FIG. 1. Monitoring system 10 is incorporated into refrigeration system 12 which includes compressor 14, condenser 16, and evaporator 18. Fluid circulates in the direction shown by arrow 20 from discharge side 22, the high-pressure side, of compressor 14 to monitoring system 10 and to condenser 16, and then through expansion valve 17 and evaporator 18 to suction side 24, the low-pressure side, of compressor 14. Monitoring system 10 can be disposed directly in line with the components of refrigeration system 12, or can be installed in a bypass line of the refrigeration system.

When acidity of the lubricating oil is to be monitored, it is desirable to place monitoring system 10 close to discharge side 22 of compressor 14 to obtain more accurate readings of acidity. The actual acidity of the oil lowers as it circulates through refrigeration system 12 due to buffering by metal components within refrigeration system 12.

Figure 2:
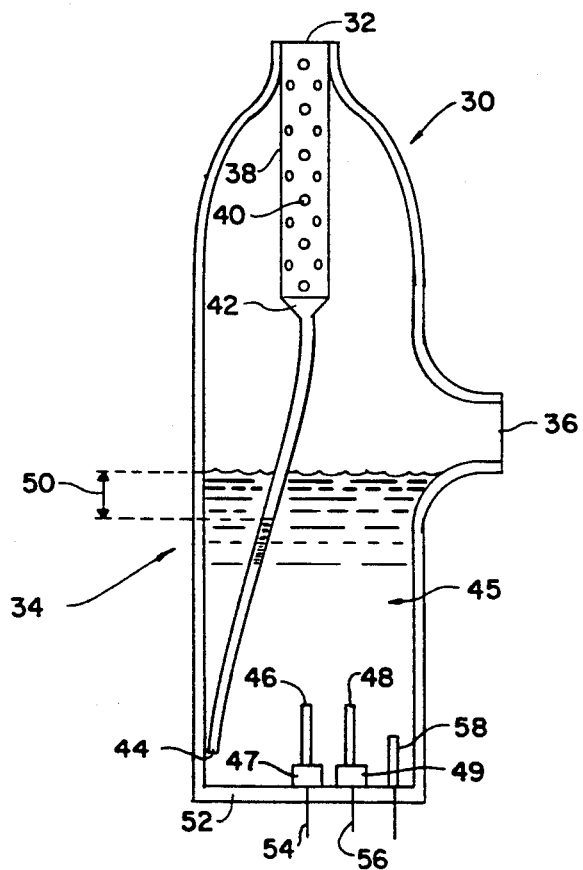
FIG. 2 is a schematic partial cutaway view of a monitoring system according to this invention.

Monitoring system 10 can include several types of housings. Housing 30, FIG. 2, includes inlet 32, reservoir 34, and outlet 36. Separator 38 is a pipe having a number of openings 40. As the refrigerant enters through inlet 32, the momentum of the entrained lubricant carries many of the droplets downwardly to intake portion 42 of reservoir 34 while the refrigerant and the remainder of the lubricant is vented through openings 40. The newly extracted lubricant travels through intake portion 42, constructed of tubing, and exits through opening 44 proximate electrodes 46, 48. Insulators 47, 49 prevent shorting between electrodes 46, 48 and plate 52 as electrically conductive particulates and other debris accumulate.

The flow of the refrigerant through housing 30 experiences a slight decrease in pressure which establishes a height differential, represented by arrow 50, in intake portion 42. The pressure drop in combination with accumulation of the most recently extracted lubricant continually forces newly extracted lubricant to the bottom of lubricant return portion 45 of reservoir 34.

The upper limit of lubricant return portion 45 is determined by the placement of outlet 36. As more lubricant is extracted, the lubricant at the top of the reservoir is forced through outlet 36. As lubricant flows through outlet 36, it is gradually re-entrained with the refrigerant passing through housing 30. Outlet 36 is oriented substantially horizontally to facilitate reentrainment. This arrangement prevents a large slug of oil from passing through the refrigeration system; such a slug could damage refrigeration system components.

In one construction, electrodes 46, 48 are plates of phosphor bronze approximately half an inch wide and an inch and one-half high, and are spaced approximately 3-4 mm (⅛ inch) from each other. This gap minimizes electrical "shorting" by carbon particles, filings, and other matter which may inadvertently appear in reservoir 34. Plate 52 threadably engages housing 30 to permit removal for maintenance and includes passages for wires 54, 56 leading from electrodes 46, 48. Temperature probe 58 monitors the temperature of the extracted lubricant and is utilized during the monitoring of resistivity as described below.

The actual dimensions of the components depends upon the type of refrigerant, the type of lubricant, and whether the housing is positioned on the suction or discharge sides of the compressor. For a flow rate of Freon-12, also known as Refrigerant-12, of 2.3 pounds per minute, and where the lubricant is Suniso 3GS oil having a density of 56.8 pounds per cubic foot, the dimensions are established as follows. The desired velocity is determined according to the formulas $$E = (NHF)/L \quad (1)$$

$$H = V^2/2g \quad (2)$$

where V is the fluid velocity in feet per second, g is the acceleration due to gravity, that is, 32.2 feet per second squared, E is the desired height differential, H is the velocity head of the refrigerant, N is the number of velocity heads, F is the vapor density of the refrigerant, and L is the lubricant density. For a desired differential of 0.3 inch, where N=1 velocity head, the velocity is determined to be 310 feet per minute (5.17 ft/sec) when the vapor density at a discharge side is 3.4 pounds per cubic foot.

The area of the openings is determined by the formulas $$\text{area} = Q/(60\ V) \quad (3)$$

and $$Q = M/F \quad (4)$$

where Q is the volumetric flow in cubic feet per minute of the refrigerant, and M is the mass flow rate in pound per minute. Q is determined to be 0.68 cubic feet per minute and the area is 0.316 square inch for this construction. Such an area can be established by a single hole having a diameter of 0.63 inch, or 20 holes having a diameter of 0.14 inch. Inlet 32 and pipe 38, FIG. 2, therefore have an inside diameter of 0.63 inch and holes 40 have a diameter of 0.14 inch to establish height 50 as 0.3 inch when housing 30 is installed on the discharge side of the compressor.

On the suction side of the compressor, the refrigerant has a density of 0.9 pound per cubic foot. According to equations (1)-(3), velocity V is determined to be 600 feet per minute, volumetric flow rate Q is determined to be 2.5 cubic feet per minute, and the area is 0.60 square inch. The diameter for a single opening is 0.87 inch and, for twenty holes, each hole must have a diameter of 0.195 inch. Such a construction establishes a small pressure drop across it of 0.01 pound per square inch.

The oil content of the refrigerant circulating through a relatively new compressor typically amounts to 0.5%, but values in excess of 1% are observed in well-worn compressors that have been in service for a number of years. For a mass flow rate of refrigerant of 2.3 pounds per minute, the mass flow rate of the entrained oil is 0.012 pound per minute. Based on an extraction efficiency of 20%, 0.002 pound per minute, that is, 1.0 ml per minute, accumulates in the reservoir. For a reservoir capacity of 150 ml, the oil is completely replaced every 150 minutes.

Figure 3:
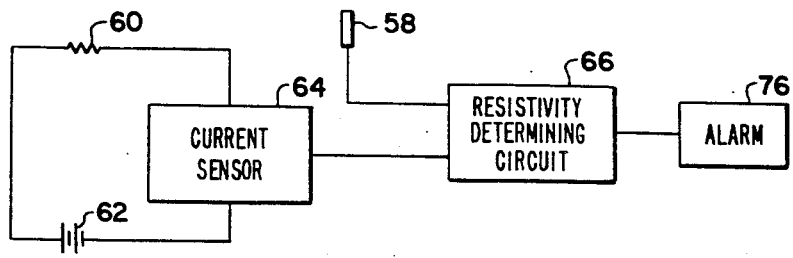
FIG. 3 is a schematic partial diagram of a monitoring system according to this invention having elements for determining the resistance between the electrodes shown in FIG. 2.

The resistance between electrodes 46, 48 is represented by resistor 60, FIG. 3. A voltage is applied across resistor 60 by voltage source 62 and a resulting current is measured by current sensor 64. The resistivity of resistor 60 is determined by circuit 66 by calculating resistance from the known voltage and the measured current. The voltage is typically 200 volts which results in a picoamp current level.

Figure 4:
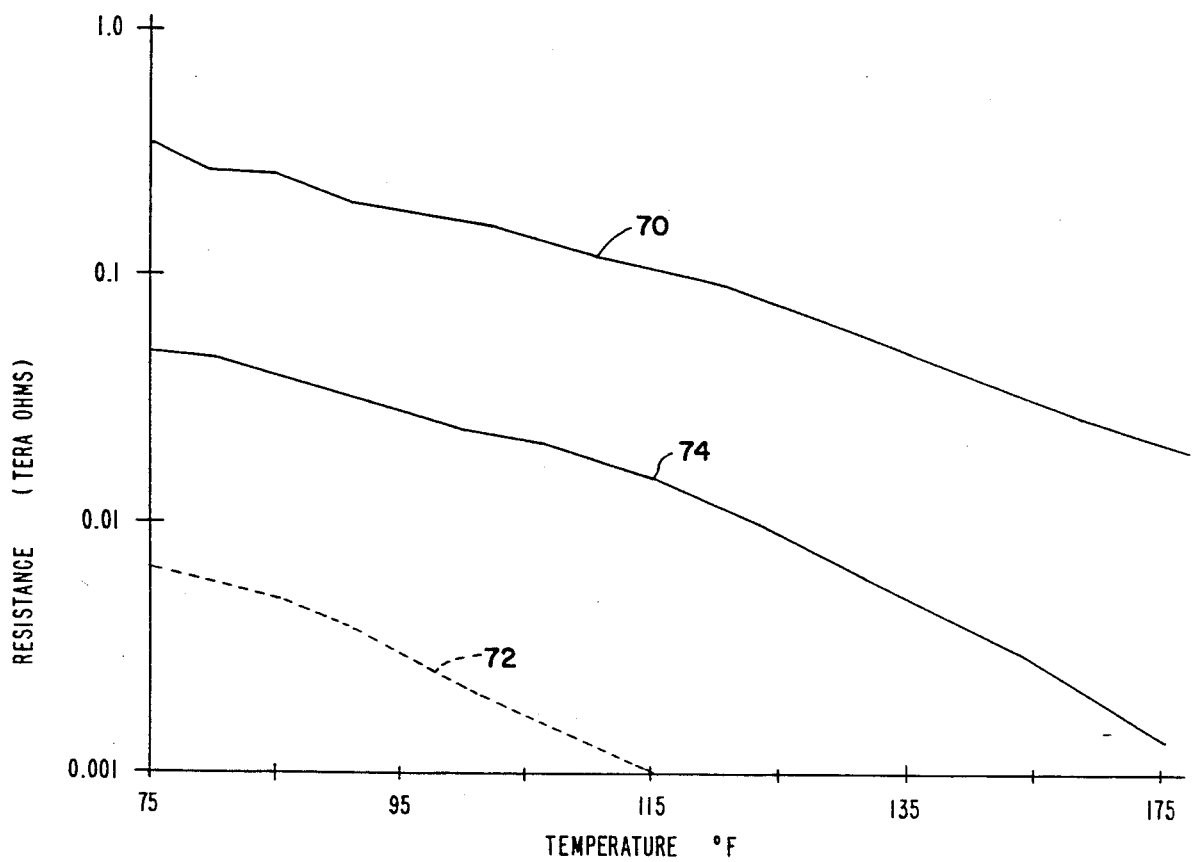
FIG. 4 is a chart showing the difference between the resistance of clean and contaminated oil.

The relative difference in resistivity of clean and contaminated oil as a function of temperature is shown in FIG. 4 for one particular electrode configuration. New Suniso 3GS oil was measured to have a resistivity of 0.5 tera ohms to tens of giga ohms in relation to temperature as shown by curve 70. Heavily contaminated Suniso 3GS oil exhibited the relationship shown by curve 72.

Because resistance does vary according to temperature, temperature probe 58 provides temperature information to resistivity determining circuit 66, FIG. 3, when the operating temperature is not known. Circuit 66 adjusts the measured resistance to compensate for changes in resistivity attributable to changes in temperature.

When the resistivity drops below a predetermined threshold such as that represented by curve 74, FIG. 4, alarm 76, FIG. 3, is activated to sound a warning bell or to shut down the refrigeration system. Alternatively, alarm 76 is a digital display which indicates resistance and temperature. In yet another construction, circuit 66 is a comparator which simply determines a rise in current above a certain threshold to detect a change in resistivity of the lubricant.

Chemical changes occur over time as the refrigerant degrades. Many of these changes cause an increase in acidity, but resistivity measurements by electrodes proved to be far more sensitive to increases in acidity than wet chemical titrations. As one example, samples of new and contaminated Suniso 3GS oil were measured at 70 degrees F. The new oil had a resistivity of 500 giga ohms and an acid number of 0.015. The contaminated oil, obtained from a compressor which had overheated, had a resistivity of 30 M ohms and an acid number of only 0.061. In other words, the resistivity varied by four orders of magnitude while the acid number remained within the same order of magnitude. Further, as noted above, determining the acid number of contaminated oil by chemical titration becomes increasingly difficult as the oil becomes contaminated.

An alternative monitoring system is shown in FIG. 5 which utilizes the orientation between inlet 82 and outlet portion 84 of housing 80 to separate the entrained oil. A velocity of 300 feet per minute for refrigerant directed downwardly separates some of the oil from the vapor stream when outlet portion 84 is oriented approximately 90 degrees relative to inlet 82.

Lower housing 86 is cut away to reveal electrodes 88, 90 having insulators 92, 94, respectively. Newly extracted oil arrives at the top of intake portion 95 of reservoir 97. Sight glass 96 includes front window 98 and a rear window (not shown) so that personnel can monitor the electrodes to ensure that they have not become fouled or shorted by a metal filing. Plate 106 is threaded so that the electrodes can be easily cleaned, particularly when the oil is changed. Further, a drain port 99 is provided in return portion 100 to enable conventional chemical testing.

To establish a turnover of oil, return portion 100 draws liquid from the lower region of intake portion 95 and passes the lubricant downstream of opening 85 of outlet portion 84 to enable the lubricant to become re-entrained with the refrigerant. Arrow 102 represents the differential between the level of the lubricant in intake portion 95 and opening 104 of return portion 100. As was shown above for housing 30, FIG. 2, the passageways will be somewhat larger within housing 80 when the monitoring system is disposed on the suction side of the compressor.

The ability of an apparatus according to this invention to remove a liquid from a gas depends on a number of factors including the solubility of the gas in the liquid, the viscosity of the liquid, the surface tension of the liquid, the density of liquid, and the vapor pressure of the liquid. Refrigerant-12 is highly soluble in refrigeration oils, refrigerant-22 is moderately soluble, and ammonia is highly insoluble in oil.

The viscosity of oil increases dramatically with decreases in temperature. A more viscous liquid separates more readily from a gas than a liquid of lesser viscosity. The temperature of refrigerant-12 at the discharge side of the compressor is typically 200 degrees Fahrenheit while the temperature at the suction side is about 60 degrees Fahrenheit. It is therefore more difficult to extract lubricant from the discharge side of the compressor.

The surface tension and density of most liquids increase as temperature decreases. Therefore, larger drops of liquid are sustained by surface tension at 60 degrees Fahrenheit than at 200 degrees Fahrenheit, and the liquid drops are heavier at the lower temperature. Heavier drops are easier to separate by centrifugal forces. Further, because the vapor pressure of most liquids increases with temperature, at higher temperatures liquid has more of its mass in vapor form.

More rigorous separation techniques are required when the liquid and gas are highly soluble, or when the temperatures are relatively high. Monitoring system 110 according to this invention, FIG. 6, is highly efficient at extracting liquid from a fluid. Fluid exiting from inlet pipe 112 makes an 180 degree turn and passes through annulus 114 of housing 116. Approximately two velocity heads of pressure are lost during the turn, and another velocity head is lost during the change from the circular to an annular flow pattern within housing 116. Additional liquid is separated when droplets strike lip 117. The fluid then makes a 90 degree turn during entry of opening 118 in outlet portion 120. Two velocity heads are lost at this point, one due to the 90 degree turn and the other to the change from an annular to a circular flow pattern. An additional velocity head is lost at elbows 122, 124 of outlet 120. Therefore, approximately seven velocity heads are lost between opening 126 of intake portion 128 and opening 130 of return portion 132. Arrow 134 represents the significant height differential caused by the pressure drop of the flowing fluid. In one construction, inlet 112 and outlet portion 120 are constructed of pipe having an inner diameter of 0.545 inch and portion 115 of housing 116 has an inner diameter of 1.265 inch. Annulus 114 has a cross-sectional area of 0.95 square inch. Height differential 134 is 2.7 inch when monitoring system 110 is installed on the discharge side of the compressor having refrigerant-12 vapor as described above.

In this construction, monitoring system 110 includes thermal insulation 135, sight glasses 136 and 138, electrodes 140, 142, drain valve 144, and restriction valve 146. Restriction valve 146 is provided to dampen momentary surges in pressure which could force an excessive amount of extracted liquid through opening 130. Valve 146 can be a fixed orifice or an adjustable valve to selectively dampen pressure surges. Similarly, a restriction can be provided at opening 44 of intake portion 42, FIG. 2.

The relationship between intake portion 128 and return portion 132 of reservoir 129 is shown schematically in FIG. 7. Because extracted liquid 150 is relatively incompressible, height differential 134 is established when pressure $p_1$ at opening 126 is greater than pressure $p_2$ at opening 130. While a difference in height of a liquid in a conduit exposed to two different pressures is used conventionally as a manometer, an apparatus according to the present invention utilizes the pressure differential to pump liquid, that is, to propel extracted liquid through the reservoir. As shown in FIG. 7, each additional unit of liquid added through opening 126 results in an equal unit of liquid being expelled through opening 130 so that liquid 150 is continually replaced. In other words, trap volume 152 remains constant.

Figure 8A:
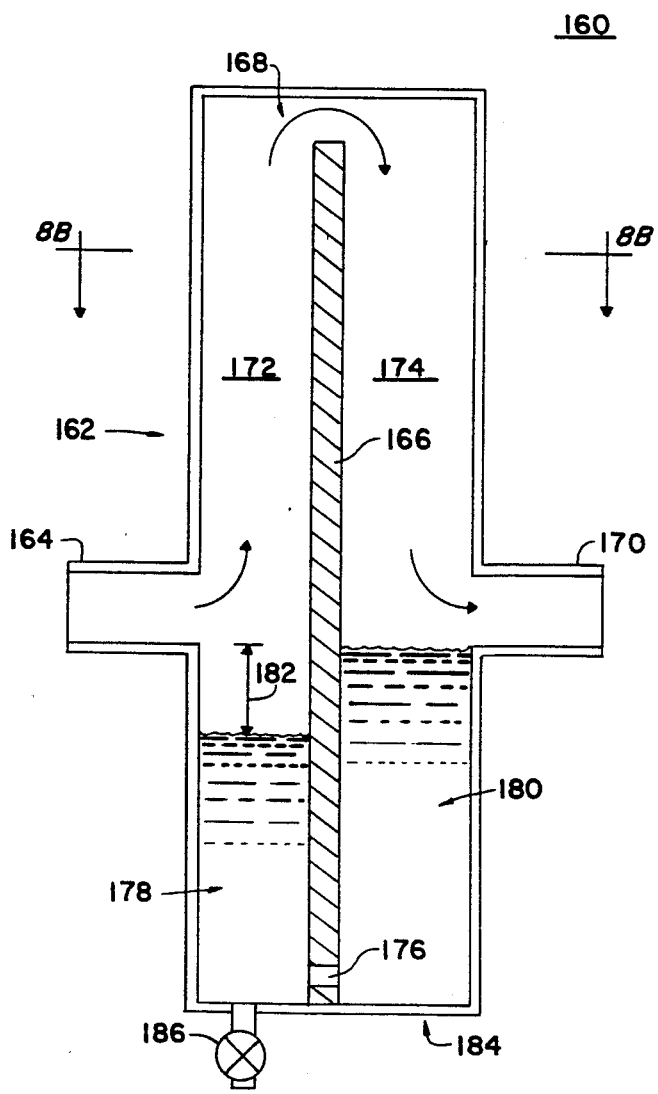
FIG. 8A is a schematic cross-sectional diagram of a further apparatus according to this invention.
Figure 8B:
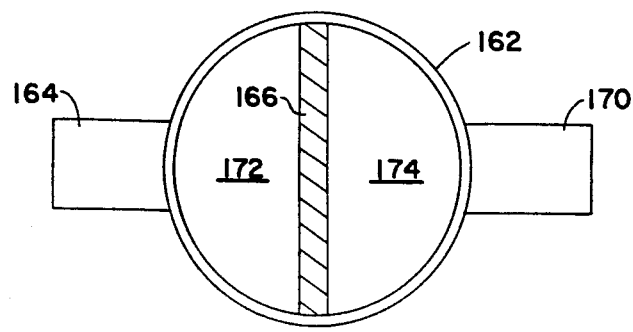
FIG. 8B is a schematic cross-sectional view along lines 8B—8B of FIG. 8A.

Apparatus 160 according to this invention, FIG. 8A, also establishes a pressure drop of approximately seven velocity heads and accomplishes the pressure drop entirely within housing 162. Fluid enters inlet 164 and is guided by barrier 166 through opening 168 and to outlet 170. As shown in FIG. 8B, barrier 166 completely separates volume 172 from volume 174 except at opening 168 and at orifice 176, FIG. 8A. Intake portion 178 communicates with return portion 180 through orifice 176. Arrow 182 represents the height differential between the extracted liquid for the two portions of reservoir 184. Valve 186 enables extracted liquid to be withdrawn for sampling. Alternatively, electrodes are provided in reservoir 184 as described above. Orifice 176 may be replaced by an external restriction valve to provide variable damping capability.

In one or more of the above-described embodiments, straightening vanes or other baffles may be added to the inlet, the outlet, or both to dampen turbulence and to increase separation efficiency. Further, the height differential of the liquid provides an accurate measurement of the pressure difference, similar to the operation of a manometer. Moreover, the term "fluid" encompasses gas, vapor and liquid.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A monitoring system, comprising:

a housing having an inlet for receiving a circulating fluid having a liquid entrained therein, a reservoir for containing extracted liquid, and an outlet portion disposed in predetermined relationship with said reservoir for venting the fluid from the housing;

a conduit extending through said inlet and into said housing, below said outlet portion, for directing the circulating fluid in a curved path past said reservoir to create a centrifugal force which separates the liquid from the fluid and directs the liquid into said reservoir; and probe means, disposed in said reservoir, for measuring an electrical parameter representative of the electrical resistance of the liquid to detect a change in resistivity indicative of contamination of the liquid.

2. The monitoring system of claim 1 in which said separating means, said reservoir and said outlet portion are arranged relative to each other to establish continual replacement of extracted liquid.

3. The monitoring system of claim 1 in which said reservoir includes an intake portion and a liquid return portion for drawing the extracted liquid from said intake portion and passing the liquid to said outlet portion to mix with the vented fluid.

4. The system of claim 1 further including lip means, disposed between said outlet portion and said reservoir, for further separating liquid entertained in said circulating refrigerant.

5. The monitoring system of claim 3 in which said housing is constructed to establish a decrease in pressure of the fluid between said intake portion and said liquid return portion to pump extracted liquid through said reservoir.

6. The monitoring system of claim 1 in which said outlet portion is constructed to reentrain the extracted liquid with vented fluid.

7. The monitoring system of claim 1 in which said probe means includes a pair of electrodes.

8. The monitoring system of claim 7 further including sight glass means for viewing said electrodes.

9. The monitoring system of claim 1 in which said separating means includes means for altering the direction of flow of the fluid from said inlet.

10. The monitoring system of claim 1 further including alarm means, responsive to said probe means, for indicating when said probe means detects a change in resistance of the extracted liquid.

11. The monitoring system of claim 1 further including means for comparing the measured electrical parameter with a reference level to detect contamination of the liquid.

12. The monitoring system of claim 1 further including means for sensing the temperature of the liquid.

13. The monitoring system of claim 12 further including means, responsive to said means for sensing, for adjusting the measured value of the electrical parameter to compensate for changes in resistivity attributable to changes in temperature.

14. A monitoring system, for use within a closed refrigeration system including a compressor, a condenser and evaporator, for detecting contamination of a lubricant entrained in a refrigerant circulating through the refrigeration system, said monitoring system comprising:

a housing having an inlet for receiving the refrigerant, a reservoir for containing extracted lubricant, and an outlet portion disposed in predetermined relationship with said reservoir for venting the refrigerant to the remainder of the refrigeration system;

a conduit extending through said inlet and into said housing, below said outlet portion, for directing the circulating refrigerant in a curved path past said reservoir to create a centrifugal force which separates the lubricant from the refrigerant and directs the lubricant into said reservoir; and probe means, disposed in said reservoir, for measuring an electrical parameter representative of the electrical resistance of the lubricant to detect a change in resistivity indicative of contamination of the lubricant.

15. The monitoring system of claim 14 in which said housing is disposed on the discharge side of said compressor.

16. The monitoring system of claim 14 in which said reservoir includes an intake portion and a lubricant return portion for drawing the extracted lubricant from said intake portion and passing the lubricant to said outlet portion to mix with the vented refrigerant.

17. The monitoring system of claim 16 in which the housing is constructed to establish a decrease in pressure of the refrigerant between the intake portion and the lubricant return portion to pump extracted lubricant through the reservoir.

18. The monitoring system of claim 14 further including means for sensing the temperature of the liquid and means, responsive to said means for sensing, for adjusting the measured value of the electrical parameter to compensate for changes in resistivity attributable to changes in temperature.

* * * * *